United States Patent [19]
Georgiev et al.

[11] Patent Number: 4,767,866
[45] Date of Patent: Aug. 30, 1988

[54] 3-PHENYL-3-(1H-1,2,4-TRIAZOL-1-YLMETHYL)-2-METHYL-5-ALKYLISOXAZOLIDINES

[75] Inventors: Vassil S. Georgiev, Rochester; George B. Mullen, Avon, both of N.Y.

[73] Assignee: Pennwalt Corporation, Philadelphia, Pa.

[21] Appl. No.: 36,831

[22] Filed: Apr. 10, 1987

[51] Int. Cl.$^4$ .................. A01N 43/653; C07D 249/08
[52] U.S. Cl. ..................................... 548/240; 548/265
[58] Field of Search ......................... 548/240

[56]         References Cited
        U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS

| | | | |
|---|---|---|---|
| 171137 | 2/1986 | European Pat. Off. | 548/215 |
| 54-76579 | 6/1979 | Japan . | |

OTHER PUBLICATIONS

Sokolov, S. V. et al., Chemical Abstract 55:7399, (1961), Abstracting, "Isoxazole Compounds III, Synthesis of Some Isoxazolylazoles", Zhur. Obshchei Khim., 30, pp. 1781–1787, (1960).
Kano, H. et al., Chem. Abstract 62:9139A, (1965), Abstracting French 1,376,432, (Oct. 23, 1964).
Kano, H. et al., Chem. Abstract 63:8367a, (1965), Abstracting French 1,380,177, (Nov. 27, 1964).
Takahi, Y. et al., Chem. Abstract 81:22233c, (1974), Abstracting Japan Kokai 7399,336, (Dec. 15, 1973).
Boyce, C. B. et al., Chem. Abstract 87:23258a, (1977), Abstracting German Offen. 2,639,189, (Mar. 10, 1977).
Funaki, Y. et al., Chem. Abstract 92:128915u, (1980), Abstracting Japan Kokai 79, 76,579, (Jun. 19, 1979).
Kelly, R. C. et al., Chem. Abstract 93:114498u, (1980), Abstracting German Offen. 2,918,878, (Nov. 22, 1979).
Haken, P. T. et al., Chem. Abstract 93:132471j, (1980), Abstracting Brit. Pat. Appln. 2,024,218, (Jan. 9, 1980).

Primary Examiner—Donald G. Daus
Assistant Examiner—Mark W. Noel

[57]            ABSTRACT

3-Phenyl-3-(1H-1,2,4-triazol-1-methyl)-2-methyl-5-alkylisoxazolidines and related derivatives in which hydrogens in the phenyl ring are replaced by halogen, lower alkyl or lower alkoxy groups are useful as antifungal agents.

5 Claims, No Drawings

3-PHENYL-3-(1H-1,2,4-TRIAZOL-1-YLMETHYL)-2-METHYL-5-ALKYLISOXAZOLIDINES

BACKGROUND OF THE INVENTION

This invention relates generally to substituted 2-methylisoxazolidines and more specifically to 3-phenyl-3-(1H-1,2,4-triazol-1-ylmethyl)-2-methyl-5-alkylisoxazolidine derivatives which are useful as antifungal agents.

BRIEF SUMMARY OF THE INVENTION

In accordance with this invention there are provided compounds of the formula:

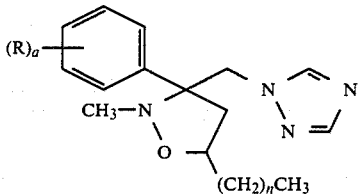

and the pharmaceutically acceptable acid addition salts thereof, in the form of their enantiomers or mixtures of their enantiomers including diastereoisomeric pairs of such enantiomers, wherein;

a=1 or 2,

R is selected from hydrogen, lower alkyl, lower alkoxy, halogen, and combinations thereof, provided that the ortho position is hydrogen, and the alkyl moiety $(CH_2)_n$ represents a branched or unbranched chain where n=1 to 18.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, N.Y., N.Y. (1980)]. The compound prepared in Example 3 below was found to have moderate inhibitory activity against trichophyton rubrum, trichophyton schoenleinii, microsporum audouini and microsporum canis (minimum inhibitory concentration, MIC, of <20 to 70 ug/ml).

Because of the antifungal activity of the compounds of the invention they can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

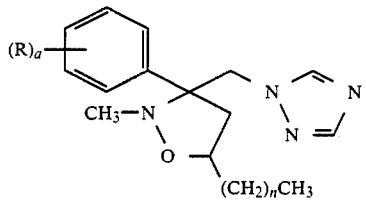

and the pharmaceutically acceptable acid addition salts thereof, in the form of their enantiomers or mixtures of their enantiomers including diastereoisomeric pairs of such enantiomers, wherein;

a=1 or 2, $R^1$ is selected from hydrogen, lower alkyl, lower alkoxy, halogen, and combinations thereof, provided that the ortho position is hydrogen, and the alkyl moiety $(CH_2)_n$ represents a branched or unbranched chain where n=1 to 18.

By halogen is meant chlorine, bromine, fluorine and iodine with chlorine and fluorine being preferred. By lower alkyl is meant such groups containing one to four (1-4) carbons and by lower alkoxy is meant such groups containing one to six (1-6) carbons. In either case such groups with three or more carbons can be a branched or unbranched chain. Compounds having ortho substitution of the phenyl group were not prepared probably due to steric hindrance.

The 3-phenyl-3-(triazol-1-ylmethyl)-2-methyl-5-alkylisoxazolidine derivatives of the invention are obtained as a mixture of cis- and trans-diastereomers due to the presence of two asymmetric carbon atoms in the isoxazolidine ring. The diastereomeric mixture is conveniently separated by flash-chromatography on silica gel using halogenated hydrocarbons (preferably dichloromethane and chloroform), alkanols (preferably methanol and ethanol), ethyl acetate and such, as eluents. The eluents may be used alone or in combinations such as the ones comprised of 95-99% halogenated hydrocarbon and 1-5% alkanol by volume. The stereochemistry of the two asymmetric carbon atoms in the isoxazolidine ring may be determined by conventional methods that include X-ray crystallography, nuclear magnetic resonance spectroscopy, circular dichroism and optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−)-tartaric acid, (+) and (−)-dibenzoyltartaric acid and the like.

The compounds of the invention can be prepared as illustrated in the following diagram. The synthesis of the nitrone precursors 1 is accomplished by reacting an appropriately substituted triazolylacetophenone with N-methylhydroxylamine as described in our copending application Ser. No. 900,856 filed Aug. 27, 1986 whose disclosure is incorporated herein by reference. Subsequent reaction of the nitrone with an appropriate 1-alkene compound 2 having 4 to 21 carbons provides a diastereomeric mixture of the desired cis- and trans-3-phenyl-3-(1H-1,2,4-triazol-1-yl)methyl-2-methyl-5-alkylisoxazolidine derivative 3.

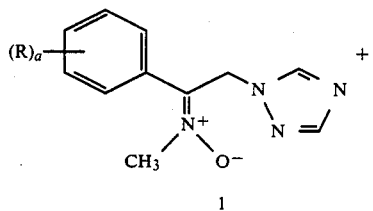

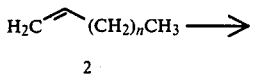

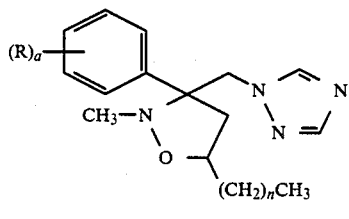

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following examples.

EXAMPLE 1

3-(4-Chlorophenyl)-3-(1H-1,2,4-triazol-1-ylmethyl)-2-methyl-5-n-hexadecylisoxazolidine (3: R=4-Cl, n=15)

A solution of 32.8 g (0.131 mol) of 1-(4-chlorophenyl)-N-methyl-2-(1H-1,2,4-triazol-1-yl)ethanimine N-oxide (1: R=4-Cl) [prepared by reacting 2-(1H-1,2,4-triazol-1-yl)-4'-chloroacetophenone (35.38 g, 0.160 mol) with N-methylhydroxylamine hydrochloride (20.0 g, 0.240 mol) and NaHCO$_3$ (20.12 g, 0.240 mol) in 500 ml ethanol] and 62.8 ml (0.196 mol) of 1-octadecene (2: n=15) in 400 ml toluene is refluxed for 48 hours under a nitrogen atmosphere. Upon cooling to room temperature the solvent is removed under reduced pressure. The residual dark solid is collected and washed sequentially with acetonitrile and ether. Crystallization from ethyl acetate gave 9.0 g (14%) of isomer A (3: R=4-Cl, n=15), melting at 100°–102° C.

Anal. Calcd for C$_{29}$H$_{47}$ClN$_4$O: C, 69.22; H, 9.42; N, 11.13; Cl, 7.05. Found: C, 69.34; H, 9.33; N, 11.05; Cl, 7.39.

EXAMPLE 2

3-Phenyl-3-(1H-1,2,4-triazol-1-ylmethyl)-2-methyl-5-n-hexylisoxazolidine (3: R=H, n=5)

Derivative 3 (R=H, n=5) is prepared by a procedure similar to that described in Example 1 by reacting 1-phenyl-N-methyl-2-(1H-1,2,4-triazol-1-yl)ethanimine N-oxide (1: R=H) with 1-octene (2: n=5). The resulting cis- and trans-diastereomeric mixture of compound 3 (R=H, n=5) is flash-chromatographed on neutral silica gel using as eluent a 98:2 by volume mixture of chloroform-methanol. Isomer A has a melting point of 93°–99° C. (ethyl acetate).

Anal. Calcd for C$_{19}$H$_{28}$N$_4$O: C, 69.48; H, 8.59; N, 17.06. Found: C, 69.45; H, 8.63; N, 17.08.

EXAMPLE 3

3-(4-Methoxyphenyl)-3-(1H-1,2,4-triazol-1-ylmethyl)-2-methyl-5-n-octylisoxazolidine (3: R=4-OCH$_3$, n=7)

Derivative 3 (R=4-OCH$_3$, n=7) is prepared by a procedure similar to that described in Example 1 by reacting 1-(4-methoxyphenyl)-N-methyl-2-(1H-1,2,4-triazol-1-yl)ethanimine N-oxide (1: R=4-OCH$_3$) with 1-decene (2: n=7). The resulting diastereomeric mixture of cis- and trans-derivative 3 (R=4-OCH$_3$, n=7) is flash-chromatographed on neutral silica gel using chloroform-methanol (99:1 by volume) as eluent. Isomer A has a melting point of 89°–91° C. (ethyl acetate).

Anal. Calcd for C$_{22}$H$_{34}$N$_4$O$_2$: C, 68.36; H, 8.87; N, 14.49. Found C, 68.48; H, 8.76; N, 14.52.

EXAMPLE 4

3-(4-Chlorophenyl)-3-(1H-1,2,4-triazol-1-ylmethyl)-2-methyl-5-n-decylisoxazolidine (3: R=4-Cl, n=9)

Derivative 3 (R=4-Cl, n=9) is prepared by a procedure similar to that described in Example 1 by reacting 1-(4-chlorophenyl)-N-methyl-2-(1H-1,2,4-triazol-1-yl)ethanimine N-oxide (1: R=4-Cl) with 1-dodecene (2: n=9). The resulting diastereomeric mixture of cis- and trans-derivative 3 (R=4-Cl, n=9) is purified by fractional crystallization using ethyl acetate as solvent. Isomer A has a melting point of 91°–94° C. (ethyl acetate).

Anal. Calcd for C$_{23}$H$_{35}$ClN$_4$O: C, 65.93; H, 8.42; N, 13.37; Cl, 8.46. Found C, 65.87; H, 8.28; N, 13.29; Cl, 8.79.

Derivative 3 where n=18 is prepared by a procedure similar to that described in Example 1 by substituting 1-heneicosene for 1-octadecene.

Other compounds of the invention where R includes mono or disubstitution with halogen, lower alkyl and-/or lower alkoxy are prepared starting with nitrones 1 formed from triazolylacetophenones such as:

2-(1H-1,2,4-triazol-1-yl)-4'-methylacetophenone
2-(1H-1,2,4-triazol-1-yl)-4'-fluoroacetophenone,
2-(1H-1,2,4-triazol-1-yl)-3',4'-dichloroacetophenone,
2-(1H-1,2,4-triazol-1-yl)-4'-chloro-3'-methylacetophenone,
2-(1H-1,2,4-triazol-1-yl)-3'-methoxyacetophenone,
2-(1H-1,2,4-triazol-1-yl)-3'-methylacetophenone.

Salts of the compounds of the inventions can be prepared as known in the art, for example, by dissolving the compound in a 10:1 by volume mixture of ethanol and aqueous acid such as HCl or HNO$_3$, evaporating the solvent, and then recrystallizing the crude salt, for example, from methanol-ether, 1:3 by volume in the case of HCl salts, and ethanol in the case of HNO$_3$ salts.

We claim:

1. A compound of the formula:

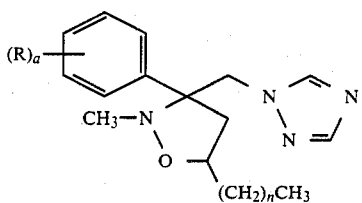

and the pharmaceutically acceptable acid addition salts thereof, in the form of their enantiomers or mixtures of their enantiomers including diastereoisomeric pairs of such enantiomers, wherein;

a=1 or 2,

R is selected from hydrogen, lower alkyl, lower alkoxy, halogen, and combinations thereof, provided that the ortho position is hydrogen, and the alkyl moiety $(CH_2)_n$ represents a chain where n=1 to 18.

2. The compound of claim 1 wherein the compound is 3-(4-chlorophenyl)-3-(1H-1,2,4-triazol-1-ylmethyl)-2-methyl-5-n-hexadecylisoxazolidine.

3. The compound of claim 1 wherein the compound is 3-phenyl-3-(1H-1,2,4-triazol-1-ylmethyl)-2-methyl-5-n-hexylisoxazolidine.

4. The compound of claim 1 wherein the compound is 3-(4-methoxyphenyl)-3-(1H-1,2,4-triazol-1-ylmethyl)-2-methyl-5-n-octylisoxazolidine.

5. The compound of claim 1 wherein the compound is 3-(4-chlorophenyl)-3-(1H-1,2,4-triazol-1-ylmethyl)-2-methyl-5-n-decylisoxazolidine.

* * * * *